(12) United States Patent
Tsubusaki et al.

(10) Patent No.: US 9,777,113 B2
(45) Date of Patent: Oct. 3, 2017

(54) PRODUCTION METHOD OF MEDICAL POLYOXYPROPYLENE POLYMER AND PRODUCTION METHOD OF MEDICAL POLYOXYPROPYLENE/POLYOXYETHYLENE BLOCK COPOLYMER

(71) Applicant: NOF CORPORATION, Tokyo (JP)

(72) Inventors: Takuma Tsubusaki, Kawasaki (JP); Yuji Yamamoto, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 0 days.

(21) Appl. No.: 15/033,303

(22) PCT Filed: Oct. 24, 2014

(86) PCT No.: PCT/JP2014/078297
§ 371 (c)(1),
(2) Date: Apr. 29, 2016

(87) PCT Pub. No.: WO2015/064487
PCT Pub. Date: May 7, 2015

(65) Prior Publication Data
US 2016/0264730 A1    Sep. 15, 2016

(30) Foreign Application Priority Data

Oct. 31, 2013   (JP) ................................. 2013-227328

(51) Int. Cl.
| | | |
|---|---|---|
| *C08G 64/00* | (2006.01) | |
| *C08G 65/08* | (2006.01) | |
| *C08G 65/26* | (2006.01) | |
| *C08G 65/30* | (2006.01) | |
| *C08G 65/331* | (2006.01) | |
| *A61L 27/18* | (2006.01) | |
| *A61L 31/06* | (2006.01) | |
| *C08G 63/02* | (2006.01) | |

(52) U.S. Cl.
CPC .............. *C08G 65/08* (2013.01); *A61L 27/18* (2013.01); *A61L 31/06* (2013.01); *C08G 65/26* (2013.01); *C08G 65/2606* (2013.01); *C08G 65/2618* (2013.01); *C08G 65/2696* (2013.01); *C08G 65/30* (2013.01); *C08G 65/331* (2013.01); *C08G 2650/58* (2013.01); *C08L 2203/02* (2013.01)

(58) Field of Classification Search
CPC .................................................... C08G 65/08
USPC ........................................................ 525/409
See application file for complete search history.

(56) References Cited

U.S. PATENT DOCUMENTS

| | | |
|---|---|---|
| 3,271,462 A | 9/1966 | Earing |
| 5,811,566 A | 9/1998 | Watabe et al. |
| 5,962,748 A | 10/1999 | Lambert |
| 5,973,096 A | 10/1999 | Watabe et al. |
| 6,207,794 B1 | 3/2001 | Yamasaki et al. |

FOREIGN PATENT DOCUMENTS

| | | |
|---|---|---|
| CN | 1094072 A | 10/1994 |
| CN | 102453244 A | 5/2012 |
| CN | 102552931 A | 7/2012 |
| EP | 0916686 A1 | 5/1999 |
| JP | 4-153219 A | 5/1992 |
| JP | 9-40769 A | 2/1997 |
| JP | 2647556 B2 | 8/1997 |
| JP | 11-106500 A | 4/1999 |
| JP | 2004-315554 A | 11/2004 |
| JP | 2007-146191 A | 6/2007 |
| JP | 2007-176847 A | 7/2007 |

OTHER PUBLICATIONS

International Search Report dated Jan. 27, 2015 issued by International Searching Authority in counterpart International Application No. PCT/JP2014/078297 (PCT/ISA/210).
Written Opinion dated Jan. 27, 2015 issued by International Searching Authority in counterpart International Application No. PCT/JP2014/078297 (PCT/ISA/237).
Mereyala et al., "Study of Metal and Acid Catalysed Deprotection of Propargyl Ethers of Alcohols via their Allenyl Ethers", Tetrahedron, vol. 55, 1999, 12 pages total.
Su et al., "Isomerization of Allyl Ethers Initiated by Lithium Diisopropylamide", Organic Letters, vol. 12 No. 23, Aug. 26, 2010, 4 pages total, American Chemical Society English.
Simons et al., "The Polymerization of Propylene Oxide", Journal of Polymer Science, vol. 44, Jan. 15, 1960, 10 pages total.
Gotoh, "Relation between Molecular Weight Distribution and Refining Process of Crude Polyether Obtained From Propylene Oxide", Journal of the Chemical Society of Japan, No. 9, 1993, 6 pages total.

(Continued)

*Primary Examiner* — Terressa Boykin
(74) *Attorney, Agent, or Firm* — Sughrue Mion, PLLC

(57) ABSTRACT

A method of producing a medical polyoxypropylene polymer and a polyoxypropylene/polyoxyethylene block copolymer including (A) adding to a polyoxypropylene polymer which is obtained by ring-opening polymerization of propylene oxide to a starting substance having an active hydrogen reacting with the propylene oxide and contains allyl ether as an impurity, a tertiary alkoxide of alkali metal in an excess amount based on a molar number of the active hydrogen of the starting substance and heat treating at 115° C. or less to isomerize the allyl ether to propenyl ether; and (B) adding a mineral acid to the product obtained in step (A) to adjust pH to 4 or less and treating at 70° C. or less to hydrolyze the propenyl ether. Also disclosed is a method of producing a medical polyoxypropylene/polyoxyethylene block copolymer which includes performing ring-opening polymerization of ethylene oxide to the polyoxypropylene polymer obtained above.

4 Claims, No Drawings

(56) References Cited

OTHER PUBLICATIONS

Communication dated Feb. 3, 2017 issued by the State Intellectual Property Office of the People's Republic of China in counterpart Chinese Patent Application No. 201480059927.0.
Extended Search Report issued Apr. 21, 2017 by the European Patent Office in counterpart European Patent Application No. 14856839.7.
Office Action dated Jun. 7, 2017 by the Japanese Patent Office in counterpart Japanese Patent Application No. 2013-227328.

PRODUCTION METHOD OF MEDICAL POLYOXYPROPYLENE POLYMER AND PRODUCTION METHOD OF MEDICAL POLYOXYPROPYLENE/POLYOXYETHYLENE BLOCK COPOLYMER

TECHNICAL FIELD

The present invention relates to production methods of a polyoxypropylene polymer and a polyoxypropylene/polyoxyethylene block copolymer. In more detail, the invention relates to production methods of a high purity polyoxypropylene polymer and a high purity polyoxypropylene/polyoxyethylene block copolymer for the purpose of being used in a medical material.

BACKGROUND ART

A polyoxyalkylene polymer obtained by ring-opening polymerization of a cyclic ether compound, for example, an alkylene oxide to a starting substance having an active hydrogen is non-antigenic, excellent in biocompatibility, and used in use, for example, a wound covering material, an antiadhesive material, a drug sustained-release material or a scaffold material in regenerative medicine, in the field of medical material. Among them, a polyoxypropylene/polyoxyethylene block copolymer is able to arbitrarily adjust swellability, flexibility, mechanical strength or cell•tissue adhesiveness by changing composition of a hydrophobic polyoxypropylene and a hydrophilic polyoxyethylene, and is widely utilized as the medical material because of its high versatility.

Production of the polyoxyalkylene polymer is ordinarily performed by ring-opening polymerization of an alkylene oxide to a starting substance having an active hydrogen in the presence of a base catalyst. However, when the ring-opening polymerization of propylene oxide is performed using a base catalyst, isomerization of propylene oxide occurs to generate allyl alcohol in parallel with the polymerization reaction of propylene oxide. The allyl alcohol generated acts as a new polymerization starting point to perform ring-opening polymerization of a propylene oxide and as a result, the polyoxypropylene polymer contains polyoxypropylene monoallyl ether.

A polyoxypropylene/polyoxyethylene block copolymer is obtained by ring-opening polymerization of ethylene oxide to a polyoxypropylene polymer. In this case, when the polyoxypropylene polymer contains polyoxypropylene monoallyl ether derived from the isomerization of propylene oxide, ethylene oxide is also polymerized from a hydroxy group of the polyoxypropylene monoallyl ether and as a result, monoallyl ether of polyoxypropylene/polyoxyethylene block copolymer is by-produced.

The presence of an unsaturated ether, for example, the ally ether, in the polyoxypropylene polymer and the polyoxypropylene/polyoxyethylene block copolymer leads to substantial decrease in hydroxy group number and in the case where the hydroxy group is subjected to chemical conversion to other functional group to use as the medical material, the function thereof is impaired. Also, the unsaturated ether is likely to exert an adverse influence on the physical property of the medical material by an unexpected surface active effect, a side reaction or the like.

It has hitherto been known that allyl ether by-produced in the ring-opening polymerization of propylene oxide is isomerized to propenyl ether by a catalytic action of the base and the propenyl ether is further hydrolyzed into propionaldehyde and a hydroxy group by an acid treatment (Non-Patent Document 1). There are many prior examples relating to decrease of an unsaturated ether (allyl ether and propenyl ether are collectively referred to as an unsaturated ether, this is also the same hereinafter) based on this methodology. However, the decrease of an unsaturated ether is not so easy in practice, and in almost all the prior examples, the unsaturated ether remains in a large amount.

For example, in Patent Document 1, a method of isomerization of allyl ether to propenyl ether using potassium hydroxide or sodium methoxide and subsequent hydrolysis of the propenyl ether is described. In the method described herein, although the treatment is conducted at 120° C. using a hydroxide of alkali metal or a primary or secondary alkoxide of alkali metal as the base catalyst, an isomerization efficiency of allyl ether to propenyl ether is low and after the subsequent hydrolysis of the propenyl ether, the unsaturated ether remains in a large amount.

As an example capable of sufficiently decreasing the unsaturated ether content, Non-Patent Document 2 is exemplified. The unsaturated ether is almost removed by treating at 160° C. for 3 hours after ring-opening polymerization of propylene oxide in the presence of about 10% by mole of potassium hydroxide based on a hydroxy group of glycerol, and then conducting a mineral acid treatment. However, according to the method described here, since it is necessary to treat at high temperature of 160° C. for a long period of time in order to isomerize allyl ether, it has a fault in that the polyoxypropylene polymer is apt to be colored. Since the colored article is recused in the field of medical material, development of a method which sufficiently decreases the unsaturated ether content and suppresses the coloring is of great significance.

On the other hand, since allyl ether is isomerized to propenyl ether also by only an acid catalyst, in Patent Document 2, the unsaturated ether content is decreased by adding a mineral acid to the polyoxypropylene polymer after the ring-opening polymerization of propylene oxide to adjust pH from 2 to 4 and then treating at 80 to 150° C. However, in the method described here the isomerization efficiency of allyl ether is low, and although there is a possibility to more decrease the unsaturated ether by treating at lower pH or high temperature, the quality degradation, for example, generation of a pungent odor occurs so that it is not adequate as the production method of the medical material.

Also, in Patent Document 3, the unsaturated ether contained in the polyoxypropylene/polyoxyethylene block copolymer is removed by gel permeation chromatography, and the polyoxypropylene/polyoxyethylene block copolymer which does not contain the unsaturated ether is used as the medical material. However, the method described here has the difficulty of applying it to an industrial scale because of problems in technical aspect and cost.

As described above, with respect to the production method of polyoxypropylene polymer and polyoxypropylene/polyoxyethylene block copolymer in which the unsaturated ether content is low and the coloring is suppressed, an example which can be easily performed on the industrial scale has not been known.

PRIOR ART DOCUMENT

Patent Document

Patent Document 1: JP-A-9-40769
Patent Document 2: JP-A-4-153219
Patent Document 3: Japanese Patent No. 2,647,556

Non-Patent Document

Non-Patent Document 1: J. Polymer Sci., 1960, 44, 303-311
Non-Patent Document 2: Journal of the Chemical Society of Japan, 1993, 9, 1085-1090

SUMMARY OF THE INVENTION

Problems that the Invention is to Solve

An object of the invention is to provide production methods of a polyoxypropylene polymer and a polyoxypropylene/polyoxyethylene block copolymer which are intended to use in the medical material and in which the unsaturated ether content is low and the coloring is suppressed.

Means for Solving the Problems

As a result of the intensive investigations to solve the object described above, the inventors have found that a polyoxypropylene polymer in which the unsaturated ether content is low and the coloring is suppressed can be obtained by adding to a polyoxypropylene polymer obtained by ring-opening polymerization of propylene oxide to a starting substance having an active hydrogen, a tertiary alkoxide of alkali metal in an excess amount based on a molar number of the active hydrogen of the starting substance to isomerize allyl ether to propenyl ether at low temperature, and then hydrolyzing the propenyl ether using a mineral acid, thereby completing the invention.

Specifically, the present invention includes the following items.
(1) A production method of a medical polyoxypropylene polymer, characterized by comprising the following steps:
(A) a step of adding to a polyoxypropylene polymer which is obtained by ring-opening polymerization of propylene oxide to a starting substance having an active hydrogen reacting with the propylene oxide and contains allyl ether as an impurity, a tertiary alkoxide of alkali metal in an excess amount based on a molar number of the active hydrogen of the starting substance and heat treating at 115° C. or less to isomerize the allyl ether to propenyl ether; and
(B) a step of adding a mineral acid to the product obtained in the step (A) to adjust pH to 4 or less and treating at 70° C. or less to hydrolyze the propenyl ether.
(2) The method of (1), characterized by performing after the step (B), at least one of (C) a step of washing the polyoxypropylene polymer with water and (D) a step of treating the polyoxypropylene polymer with an inorganic adsorbent composed of an oxide containing at least one of aluminum and silicon.
(3) A production method of a medical polyoxypropylene/polyoxyethylene block copolymer including a step of performing ring-opening polymerization of ethylene oxide to the polyoxypropylene polymer obtained by the method of (1) or (2).

Advantage of the Invention

According to the invention, the isomerization of allyl ether contained in the polyoxypropylene polymer to propenyl ether can be achieved quantitatively under a mild temperature condition and as a result, it is possible to extremely decrease the unsaturated ether content and to suppress the coloring. Therefore, the production methods according to the invention can easily provide the polyoxypropylene polymer and the polyoxypropylene/polyoxyethylene block copolymer each having high quality suitable for the medical material on the industrial scale.

MODE FOR CARRYING OUT THE INVENTION

The invention will be described in detail hereinafter.

The medical use means use to be applied to a living body, for example, a wound covering material, an antiadhesive material, a drug sustained-release material or a scaffold material in regenerative medicine.

The "starting substance having an active hydrogen reacting with propylene oxide" which can be used in the invention is a starting material for performing the ring-opening polymerization of propylene oxide. The functional group having an active hydrogen is not limited as long as it acts as a starting point of the ring-opening polymerization of propylene oxide and specifically, the starting substance preferably has a functional group selected from the group consisting of a hydroxy group, an amino group, a sulfanyl group and a carboxyl group, more preferably a hydroxy group and/or an amino group, and most preferably a hydroxy group.

As specific examples of the starting substance having a hydroxy group, alcohols described below are exemplified. As a monovalent alcohol, methanol, ethanol, propanol, isopropanol, butanol, tert-butanol, phenol and benzyl alcohol are exemplified. As a divalent alcohol, ethylene glycol, diethylene glycol, propylene glycol, water, 1,4-butanediol, 1,5-pentane diol, 1,6-hexanediol and 1,4-benzenediol are exemplified. As a polyvalent alcohol of trivalent or more, glycerol, trimethylol propane, pentaerythritol, diglycerol, N,N,N',N'-tetrakis(2-hyroxypropyl)ethylenediamine, xylitol, triglycerol, dipentaerythritol, sorbitol and hexaglycerol are exemplified. According to a preferred embodiment, a polyvalent alcohol of trivalent or more is used as the starting substance. Also, ordinarily, the valence of hydroxy groups in the polyvalent alcohol is preferably 8-valence or less.

As specific examples of the starting substance having an amino group, dimethylamine, diethylamine, piperazine, morpholine, aniline, monoethanolamine, diethanolamine, triethanolamine, ammonia, ethylenediamine, toluylenediamine and diethylenetriamine are exemplified. According to a preferred embodiment, a compound containing two or more amino groups is used as the starting substance.

A number average molecular weight per hydroxy group of the polyoxypropylene polymer obtained by ring-opening polymerization of propylene oxide to a starting substance having an active hydrogen according to the invention is preferably from 300 to 10,000, and more preferably from 500 to 5,000. Here, the number average molecular weight is a number average molecular weight converted from a hydroxyl value and is represented by 56,100×(active hydrogen number of starting substance)/(hydroxyl value).

The tertiary alkoxide of alkali metal which can be used in the step (A) of the invention is a compound wherein a hydrogen atom of a hydroxy group in a tertiary alcohol is substituted with an alkali metal.

The alkali metal constituting the tertiary alkoxide of alkali metal is preferably lithium, sodium or potassium. Also, a carbon number of the tertiary alkoxide is 4 or more, but preferably 6 or less, and more preferably 5 or less. As to specific examples of the tertiary alkoxide of alkali metal, lithium tert-butoxide, sodium tert-butoxide, potassium tert-butoxide, lithium tert-pentoxide, sodium tert-pentoxide or potassium tert-pentoxide is preferred, sodium tert-butoxide, potassium tert-butoxide, sodium tert-pentoxide or potassium tert-pentoxide is more preferred, and sodium tert-butoxide or potassium tert-butoxide is most preferred.

In order to efficiently proceed the isomerization of allyl ether to propenyl ether by an action of the tertiary alkoxide of alkali metal in the step (A) of the invention, as to the use amount of the tertiary alkoxide of alkali metal, it is necessary to use excessively than the molar number of active hydrogen of the starting substance. In the case where the use amount of the tertiary alkoxide of alkali metal is less than the molar number of active hydrogen of the starting substance, only an alkoxide of polyoxypropylene polymer is produced and the isomerization efficiency of allyl ether extremely decreases. According to a preferred embodiment, the use amount of the tertiary alkoxide of alkali metal is 1.1 times equivalent or more, more preferably 1.3 times equivalent or more, still more preferably 1.5 times equivalent or more, particularly preferably 2.0 times equivalent or more, based on the molar number of active hydrogen of the starting substance. Also, taking the necessary amount of mineral acid used in the step (B) and complexity of the post-treatment into consideration, it is preferably 5.0 times equivalent or less, and more preferably 4.0 times equivalent or less.

The treatment temperature of the step (A) in the invention is 115° C. or less, preferably 110° C. or less, more preferably 105° C. or less, and still more preferably 100° C. or less. Higher temperature than 115° C. is not preferred because the coloring becomes strong.

Also, the treatment temperature of the step (A) in the invention is preferably 70° C. or more, more preferably 80° C. or more, from the standpoint of accelerating the isomerization reaction.

As to the mineral acid which can be used in the step (B) of the invention, hydrochloric acid, sulfuric acid, sulfurous acid, nitric acid, phosphoric acid or hypophosphoric acid is preferred, hydrochloric acid, sulfuric acid or phosphoric acid is more preferred, and hydrochloric acid or sulfuric acid is still more preferred. The mineral acid can be used by diluting at an appropriate concentration.

In the step (B) of the invention, the mineral acid is added to the product obtained in the step (A) to adjust pH to 4 or less. The pH is preferably 3 or less, more preferably 2.5 or less, and still more preferably 2 or less. Also, since pH of less than 0 causes the quality degradation, for example, generation of a pungent odor, pH is preferably 0 or more, and more preferably 1 or more. In the case where the pH is more than 4, the acid concentration is poor so that the hydrolysis of propenyl ether is insufficient or the hydrolysis requires a long period of time.

The treatment temperature of the step (B) in the invention is 70° C. or less, preferably 60° C. or less, more preferably 50° C. or less, and still more preferably 40° C. or less. Also, since the treatment temperature is less than 0° C., load is applied to stirring due to increase in viscosity, deposition of neutralized salt or the like, it is preferably 0° C. or more, and more preferably 10° C. or more.

According to the invention, it is preferred to remove the excess mineral acid and the neutralized salt from the polyoxypropylene polymer after the step (B), and specifically it is preferred to remove them by at least one of step (C) and step (D). The step (C) and the step (D) may be conducted individually or in combination.

For the water washing in the step (C), water or an aqueous alkaline solution can be used. Preferred examples of the base which can be used in the preparation of aqueous alkaline solution include lithium hydroxide, sodium hydroxide, potassium hydroxide, sodium carbonate, potassium carbonate, sodium hydrogen carbonate and sodium acetate, and sodium hydroxide, potassium hydroxide, sodium carbonate, potassium carbonate, sodium hydrogen carbonate or potassium hydrogen carbonate is preferred. The bases described above may be used individually or in combination. The water washing may be conducted repeatedly.

According to a preferred embodiment of the step (C), in order to suppress the use amount of water or aqueous alkaline solution used for removing the mineral acid used in the step (B), the mineral acid is previously neutralized to around neutrality with a base and then the water washing with water or aqueous alkaline solution is performed. Specific examples of the base which can be used in the neutralization of mineral acid include lithium hydroxide, sodium hydroxide, potassium hydroxide, sodium methoxide and sodium ethoxide, and sodium hydroxide or potassium hydroxide is preferred.

The use amount of water or aqueous alkaline solution used in the water washing in the step (C) is preferably from 0.5 to 10 times by weight, more preferably from 1 to 8 times by weight, still more preferably from 2 to 6 times by weight, based on the polyoxypropylene polymer.

In the step (C), in the case where layer separation is difficult or takes a long period of time due to the emulsification phenomenon or the like, in order to improve such a problem, the water washing with adding an appropriate inorganic salt or lower alcohol may be performed. As specific examples of the inorganic salt, sodium chloride, potassium chloride, sodium bromide and potassium bromide are exemplified, and sodium chloride is preferred. The use amount of the inorganic salt is preferably from 1 to 20% by weight, more preferably from 2 to 15% by weight, still more preferably from 3 to 10% by weight, based on the water or aqueous alkaline solution used in the water washing. Also, as specific examples of the lower alcohol, methanol, ethanol, propanol, isopropanol, butanol and tert-butanol are exemplified, and methanol or ethanol is preferred.

The use amount of the lower alcohol is preferably from 0.1 to 3 times by weight, more preferably from 0.2 to 2.5 times by weight, still more preferably from 0.3 to 2 times by weight, based on the water or aqueous alkaline solution used in the water washing. The inorganic salts and the lower alcohols described above may be used individually or in combination.

Also, in the step (C), the polyoxypropylene polymer may be dissolved in an appropriate organic solvent and then the water washing is performed. As specific examples of the organic solvent, an aprotic solvent, for example, toluene, benzene, xylene, ethyl acetate, hexane, diethyl ether, tert-butyl methyl ether, tetrahydrofuran, chloroform or dichloromethane is exemplified, and toluene, ethyl acetate, tert-butyl methyl ether, chloroform or dichloromethane is preferred, and chloroform or dichloromethane is more preferred. The use amount of the organic solvent is preferably from 0.5 to 10 times by weight, more preferably from 1 to 8 times by weight, still more preferably from 2 to 6 times by weight, based on the polyoxypropylene polymer. The organic solvents described above may be used individually or in combination.

The inorganic adsorbent composed of an oxide containing at least one of aluminum and silicon, which can be used in the step (D), is an oxide containing either one or both of aluminum and silicon. Specifically, aluminum oxide, silicon dioxide, a composite oxide of aluminum oxide and silicon dioxide, a composite oxide of aluminum oxide and other metal and a composite oxide of silicon dioxide and other metal are exemplified. Other metal as is defined here includes sodium, magnesium and calcium.

In the step (D), in order to remove the excess mineral acid, an adsorbent having an acidic substance adsorption ability is preferred, and specific examples thereof include KYOWAARD 300 ($2.5MgO.Al_2O_3.0.7CO_3.nH_2O$), KYOWAARD 500 ($Mg_6Al_2(OH)_{16}(CO_3).4H_2O$), KYOWAARD 1000 ($Mg_{4.5}Al_2(OH)_{13}(CO_3).3.5H_2O$) of KYOWAARD series produced by Kyowa Chemical Industry Co., Ltd and the like. Also, in order to remove the neutralized salt, an adsorbent having a high salt adsorption ability is preferred, and specific examples thereof include KYOWAARD 2000 ($4.5MgO.Al_2O_3$), KYOWAARD 200B ($Al_2O_3.2.0H_2O$) and the like. The adsorbents may be used individually or in combination.

Also, according to the step (D) in the invention, a slightly remaining base after removing the mineral acid in the step (C) can be removed. Specific examples of the adsorbent which can be used for the purpose include an adsorbent having a basic substance adsorption ability, for example, KYOWAARD 600 ($MgO.3SiO_2.nH_2O$) or KYOWAARD 700 ($Al_2O_3.9SiO_2.nH_2O$), and KYOWAARD 700 ($Al_2O_3.9SiO_2.nH_2O$) is preferred. The adsorbents may be used individually or in combination with other adsorbents.

Further, according to the step (D) in the invention, the coloring component slightly generated in the step (A) and the step (B) can be removed. Specific examples of the adsorbent which can be used for the purpose include a dye adsorbent, for example, KYOWAARD 500 ($Mg_6Al_2(OH)_{16}(CO_3).4H_2O$) or KYOWAARD 1000 ($Mg_{4.5}Al_2(OH)_{13}(CO_3).3.5H_2O$), and KYOWAARD 1000 ($mg_{4.5}Al_2(OH)_{13}(CO_3).3.5H_2O$) is preferred. The adsorbents may be used individually or in combination with other adsorbents.

The use amount of the inorganic adsorbent in the step (D) of the invention is preferably 10% by weight or less, more preferably 8% by weight or less, still more preferably 5% by weight or less, based on the polyoxypropylene polymer. The use amount exceeding 10% by weight is not preferred because load is applied to the filtration operation and also the filter cake increases.

Although the step (D) is effective for removing the small amount of coloring component slightly generated in the step (A) and the step (B), the effect on the coloring component generated by the high temperature treatment of unsaturated ether shown in the comparative example is limited and a considerable amount of the coloring component remains without removal. Specifically, it can be said that it is impossible to decrease the coloring to such an extent that the invention can achieve only by applying the step (D).

By performing ring-opening polymerization of ethylene oxide to the polyoxypropylene polymer obtained according to the invention, a polyoxypropylene/polyoxyethylene block copolymer in which the unsaturated ether content is low and the coloring is suppressed can be produced.

In the polyoxypropylene/polyoxyethylene block copolymer according to the invention, a number average molecular weight per hydroxy group of the polyoxyethylene moiety is preferably from 600 to 20,000, and more preferably from 1,000 to 10,000. Here, the number average molecular weight of the polyoxyethylene moiety can be obtained by subtracting the number average molecular weight of the polyoxypropylene polymer before the polymerization of ethylene oxide from the number average molecular weight of the polyoxypropylene/polyoxyethylene block copolymer converted from the hydroxyl value.

As to the degree of coloring, a value evaluated by Hazen color number is used. The Hazen color number is a color number determined by comparing transparent colors of a Hazen standard colorimetric solution prepared by using a mixed solution of chloroplatinic acid and cobalt chloride and the sample as described in JIS K 0071. Also, the Hazen color number can be measured using a Hazen color number measuring instrument. As the value of Hazen color number increases, the color turns from colorless to yellow, brown and dark brown. The Hazen color number of the polyoxypropylene polymer or the polyoxypropylene/polyoxyethylene block copolymer according to the invention is preferably 100 or less, more preferably 80 or less, still more preferably 60 or less, and particularly preferably 40 or less.

EXAMPLE

The invention will be described more specifically with reference to the examples and comparative examples, but the invention should not be construed as being limited thereto.

Here, the degree of coloring is indicated by the Hazen color number. The unsaturated ether content is measured by $^1$H-NMR and indicated as milliequivalent (meq/g, also the same hereinafter) of the unsaturated ether per g of the polyoxypropylene polymer or the polyoxypropylene/polyoxyethylene block copolymer.

The degree of coloring was evaluated by comparing transparent colors of a solution prepared by diluting 4 times in weight the sample with special grade ethanol (99.5) produced by Kanto Chemical Co., Inc. and a Hazen standard colorimetric solution described in JIS K 0071.

In the $^1$H-NMR analysis, JNM-ECP400 or JNM-ECA600 produced by Jeol Datum Co., Ltd. was used, and φ5 mm tube was used. The measurement was performed by using $CDCl_3$ or $CD_3OD$ as a deuterated solvent and tetramethylsilane (TMS) as an internal standard substance.

The unsaturated ether content was calculated according to the calculation formula shown below taking the integral values of a methyl signal (near 1.1 ppm) of oxypropylene repeating unit, a methylene signal (near 5.1 to 5.3 ppm) of allyl ether terminal and a methyl signal (near 1.55 ppm) of propenyl ether terminal in the polyoxypropylene polymer as $I_1$, $I_2$ and $I_3$, respectively.

Unsaturated ether content (meq/g)=$[(I_2/2)+(I_3/3)]/(I_1/3)\times(Mn-60.10)/58.08\times10^3/Mn$ Here, the values calculated for only $I_2$ and only $I_3$ denote the allyl ether content and the propenyl ether content, respectively. Mn represents a number average molecular weight converted from the hydroxyl value of the sample, 60.10 represents a molecular weight of ethylenediamine, and 58.08 represents a molecular weight of propylene oxide.

As to the polyoxypropylene/polyoxyethylene block copolymer, the unsaturated ether content was calculated according to the calculation formula shown below taking a number average molecular weight converted from the hydroxyl value of the polyoxypropylene polymer before the polymerization of ethylene oxide and a number average molecular weight converted from the hydroxyl value of the polyoxypropylene/polyoxyethylene block copolymer after the polymerization of ethylene oxide as Mn and Mn', respectively.

Unsaturated ether content (meq/g)=$[(I_2/2)+(I_3/3)]/(I_1/3)\times(Mn-60.10)/58.08\times10^3/Mn'$ The polyoxypropylene polymer used in the examples and comparative examples was synthesized according to the propylene oxide polymerization reaction shown below.

Synthesis Example 1

Into a 5-L autoclave container were charged 146.2 g (0.500 mol) of N,N,N',N'-tetrakis(2-hydroxypropyl)ethylenediamine, 9.87 g (88.0 mmol) of a 50% by weight aqueous potassium hydroxide solution and 730 g of toluene, the air in the system was replaced by nitrogen, and then the temperature was raised to 110° C. to remove water by azeotropy with toluene. At 110° C. or less and at 0.5 Mpa or less, 2,325 g (40.0 mol) of propylene oxide was added thereto, and the reaction was continued at the same temperature more than 2 hours until the pressure in the container reached equilibrium. After removing the unreacted propylene oxide gas under a reduced pressure, polyoxypropylene polymer was obtained as colorless and transparent, low viscosity liquid.

Example 1

Into a 1-L four-necked flask equipped with a thermometer, a nitrogen inlet tube, a stirrer, a Dean-Stark tube and a condenser tube were charged 300 g (60.0 mmol) of the polyoxypropylene polymer obtained by the propylene oxide polymerization reaction and 300 g of toluene, and the temperature was raised to 110° C. under nitrogen atmosphere to remove water by azeotropy with toluene. After cooling to room temperature, 53.9 g (480 mmol) of potassium tert-butoxide in the form of slurry with 90 g of dehydrated toluene was added, and the reaction was performed at 100° C. under nitrogen atmosphere for 2 hours. After cooling to 40° C., 80 g of ion-exchanged water was gradually added thereto while continuing cooling. After adjusting pH to 1.5 by adding 120 ml (720 mmol) of 6N hydrochloric acid, the reaction was performed at 40° C. under nitrogen atmosphere for 2 hours. After neutralizing with 14 ml (140 mmol) of a 400 g/l aqueous sodium hydroxide solution with cooling, 600 g of a 5% by weight aqueous sodium chloride solution, 450 g of methanol and 600 g of chloroform were added thereto, followed by washing by a separatory funnel. The aqueous layer was discarded, and the organic layer was washed with a mixed solution of 600 g of an aqueous 5% by weight sodium chloride/5% by weight sodium hydrogen carbonate solution and 450 g of methanol and then, the solvent of the organic layer was distilled off. After removing water included in the residue by azeotropy with toluene, 9 g of KYOWAARD 700 and 9 g of KYOWAARD 1000 produced by Kyowa Chemical Industry Co., Ltd. in the form of slurry with 300 g of toluene were added, followed by stirring at 40° C. under nitrogen atmosphere for one hour. After filtering with No. 5A filter paper produced by Toyo Roshi Kaisha, Ltd., the solvent was distilled off to obtain polyoxypropylene polymer as colorless and transparent, low viscosity liquid.

Example 2

Into a 5-L autoclave container were charged 250 g (50.0 mmol) of the polyoxypropylene polymer obtained in Example 1, 282 g of toluene and a mixed solution of 1.56 g (13.9 mmol) of a 50% by weight aqueous potassium hydroxide solution and 5.5 g of methanol, the air in the system was replaced by nitrogen, and then the temperature was raised to 110° C. to remove water and methanol by azeotropy with toluene. At 120° C. or less and at 0.5 Mpa or less, 500 g (11.4 mol) of ethylene oxide was added thereto, and the reaction was continued at the same temperature more than 2 hours until the pressure in the container reached equilibrium. After removing the unreacted ethylene oxide gas under a reduced pressure, the reaction product was cooled to 80° C. and neutralized with 85% by weight phosphoric acid to obtain a polyoxypropylene/polyoxyethylene block copolymer as a nearly colorless solid.

For reference, chemical formulae corresponding to the synthesis example of polyoxypropylene polymer and Examples 1 and 2 described above are shown.

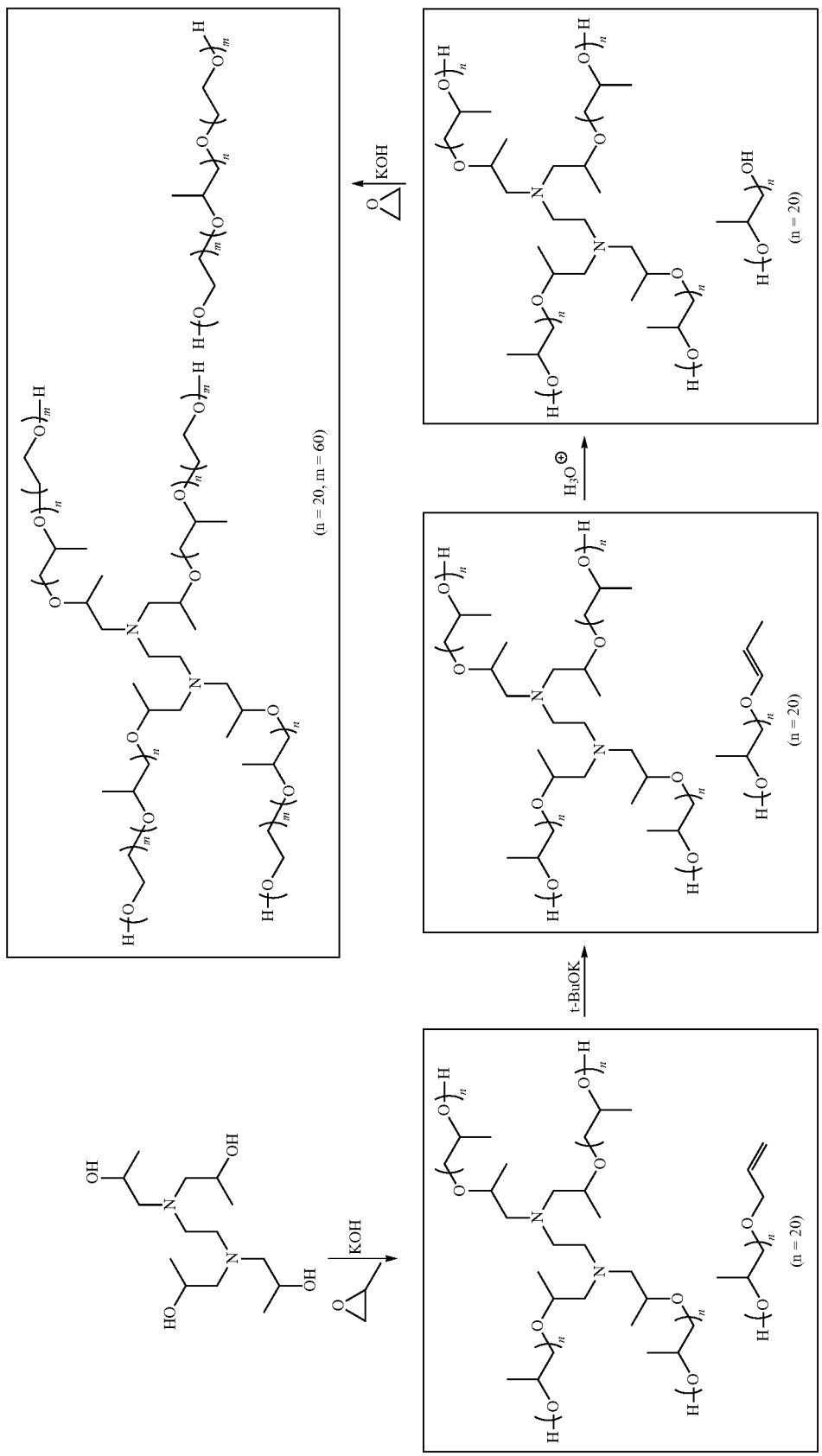

Comparative Example

The comparative experiments shown below were performed based on Non-Patent Document 2 which was considered to be the lowest unsaturated ether content in the prior art.

Comparative Example 1

Into a 1-L four-necked flask equipped with a thermometer, a nitrogen inlet tube, a stirrer, a Dean-Stark tube and a condenser tube were charged 360 g (72.0 mmol) of the polyoxypropylene polymer obtained by a polymerization reaction of propylene oxide, 360 g of toluene and 1.62 g (14.4 mmol) of a 50% by weight aqueous potassium hydroxide solution, and the temperature was raised to 110° C. under nitrogen atmosphere to remove water by azeotropy with toluene. After distilling off the total amount of toluene, the reaction was performed at 160° C. under nitrogen atmosphere for 3 hours. After cooling to 40° C., pH was adjusted to 3 with 50% by weight phosphoric acid and the reaction was performed at 100° C. under nitrogen atmosphere for one hour. After cooling to 40° C., the product was divided into three portions to use experiments of Comparative Examples 2 to 5.

Comparative Example 2

Into a 300-ml four-necked flask equipped with a thermometer, a nitrogen inlet tube, a stirrer, a Dean-Stark tube and a condenser tube were charged 120 g (24.0 mmol) of the polyoxypropylene polymer obtained in Comparative Example 1, 2.5 g of ion-exchanged water, 1.8 g of KYOWAARD 600 and 0.6 g KYOWAARD 700 produced by Kyowa Chemical Industry Co., Ltd. and the mixture was stirred at 100° C. under nitrogen atmosphere for one hour. After cooling to 40° C. and filtering with No. 5A filter paper produced by Toyo Roshi Kaisha, Ltd., the solvent was distilled off to obtain polyoxypropylene polymer as brown and transparent, low viscosity liquid.

Comparative Example 3

Into a separatory funnel were charged 120 g (24.0 mmol) of the polyoxypropylene polymer obtained in Comparative Example 1, 120 g of toluene and 120 g of ion-exchanged water, the mixture was sufficiently shaken at room temperature and then allowed to stand to separate the liquids. After removing the aqueous layer of the lower layer, the same amount of ion-exchanged water was again charged to repeat the same operation. Next, the aqueous layer was removed, the organic layer of the upper layer was concentrated under a reduced pressure to remove the remaining water by azeotropy, and then filtered with No. 5A filter paper produced by Toyo Roshi Kaisha, Ltd. to obtain polyoxypropylene polymer as brown and transparent, low viscosity liquid.

Comparative Example 4

120 g (24.0 mmol) of the polyoxypropylene polymer obtained in Comparative Example 1 was neutralized with a 400 g/l aqueous sodium hydroxide solution according to Example 1, dissolved in 240 g of chloroform, and 240 g of a 5% by weight aqueous sodium chloride solution and 180 g of methanol were added thereto, followed by washing by a separatory funnel. The aqueous layer was discarded, and the organic layer was washed with a mixed solution of 240 g of an aqueous 5% by weight sodium chloride/5% by weight sodium hydrogen carbonate solution and 180 g of methanol and then, the solvent of the organic layer was distilled off. After removing water included in the residue by azeotropy with toluene, 3.6 g of KYOWAARD 700 and 3.6 g of KYOWAARD 1000 produced by Kyowa Chemical Industry Co., Ltd. in the form of slurry with 120 g of toluene were added, followed by stirring at 40° C. under nitrogen atmosphere for one hour. After filtering with No. 5A filter paper produced by Toyo Roshi Kaisha, Ltd., the solvent was distilled off to obtain polyoxypropylene polymer as yellow and transparent, low viscosity liquid.

Comparative Example 5

Into a 5-L autoclave container was charged 100 g (20.0 mmol) of the polyoxypropylene polymer obtained in Comparative Example 1, 113 g of toluene and a mixed solution of 0.62 g (5.5 mmol) of a 50% by weight aqueous potassium hydroxide solution and 2.2 g of methanol, the air in the system was replaced by nitrogen, and then the temperature was raised to 110° C. to remove water and methanol by azeotropy with toluene. At 120° C. or less and at 0.5 Mpa or less, 200 g (4.5 mol) of ethylene oxide was added thereto, and the reaction was continued at the same temperature more than 2 hours until the pressure in the container reached equilibrium. After removing the unreacted ethylene oxide gas under a reduced pressure, the reaction product was cooled to 80° C. and neutralized with 85% by weight phosphoric acid to obtain a polyoxypropylene/polyoxyethylene block copolymer as a brown solid.

Comparative Example 6

Into a 300-ml four-necked flask equipped with a thermometer, a nitrogen inlet tube, a stirrer, a Dean-Stark tube and a condenser tube were charged 100 g (20.0 mmol) of the polyoxypropylene polymer obtained by the propylene oxide polymerization reaction and 100 g of toluene, and the temperature was raised to 110° C. under nitrogen atmosphere to remove water by azeotropy with toluene. After cooling to room temperature, 30.9 g (160 mmol) of SM-28 (28% by weight sodium methoxide methanol solution) produced by Kawaken Fine Chemical Co., Ltd. was added, and methanol was removed while raising temperature to 100° C. Subsequently, the reaction was performed at 100° C. under nitrogen atmosphere for 2 hours.

TABLE 1

| | | Hazen Color Number | Unsaturated Ether Content ($\times 10^{-3}$ meq/g) | | Allyl/Propenyl Ratio |
|---|---|---|---|---|---|
| | Analysis Point | | Allyl | Propenyl | |
| Polyoxypropylene Polymer before Treatment | | 10 or less | 30.1 | 4.0 | 88/12 |
| Example 1 | After Step (A) | — | 0 | 33.4 | 0/100 |
| | After Step (B) | — | 0 | 0 | 0/0 |
| | After Steps (C) and (D) | 10 or less | 0 | 0 | 0/0 |
| 2 | After EO Polymerization | 15 | 0 | 0 | 0/0 |

TABLE 1-continued

| | | Analysis Point | Hazen Color Number | Unsaturated Ether Content ($\times 10^{-3}$ meq/g) | | Allyl/Propenyl Ratio |
|---|---|---|---|---|---|---|
| | | | | Allyl | Propenyl | |
| Comparative Example | 1 | After High Temperature Treatment | — | 5.2 | 27.7 | 16/84 |
| | | After Acid Hydrolysis | — | 5.4 | 3.8 | 59/41 |
| | 2 | After Adsorbent Treatment | 500 or more | 5.1 | 3.5 | 59/41 |
| | 3 | After Water Washing | 500 or more | 5.5 | 3.7 | 60/40 |
| | 4 | After Step (D) | 120 | 5.7 | 4.1 | 58/42 |
| | 5 | After EO Polymerization | 500 or more | 1.9 | 1.5 | 56/44 |
| | 6 | After Sodium Methoxide Treatment | — | 30.0 | 4.0 | 88/12 |

As shown in Table 1, the polyoxypropylene polymer obtained in Example 1 had the Hazen color number of 10 or less and was almost colorless.

On the other hand, in Comparative Examples 2 and 3 including the high temperature treatment of Comparative Example 1 and the subsequent acid hydrolysis, the Hazen color number was 500 or more and the coloring was strong, and further the unsaturated ether content was large.

Also, in Comparative Example 4 wherein the post-treatment was performed by the step (D) same as in Example 1, the coloring was somewhat decreased, but it was impossible to decrease the coloring to the level equivalent to Example 1. Therefore, it is believed that the coloring generated in Comparative Example 1 contains the component which cannot be removed by the step (D) same as in Example 1.

Comparing Example 2 and Comparative Example 5 wherein ethylene oxide was ring-opening polymerized to the polyoxypropylene polymer of Example 1 and Comparative Example 2 in Table 1, respectively, the coloring of the polyoxypropylene/polyoxyethylene block copolymer obtained is clearly strong in Comparative Example 5 and suggests that the coloring of the polyoxypropylene polymer before the polymerization of ethylene oxide affects largely.

Also, in Comparative Example 6 in Table 1 wherein sodium methoxide described in Patent Document 1 was used in place of potassium tert-butoxide used in Example 1 in the same molar number and the treatment was performed at the same temperature, the isomerization of allyl ether to propenyl ether did not proceed.

Although the invention has been described in detail by reference to specific embodiments, it is apparent to those skilled in the art that it is possible to perform various alterations and modifications insofar as the alterations and modifications do not deviate from the spirit and the scope of the invention.

This application is based on a Japanese patent application filed on Oct. 31, 2013 (Japanese Patent Application No. 2013-227328), and the whole contents thereof are incorporated herein by reference. Also, all the references cited herein are incorporated as a whole.

The invention claimed is:

1. A production method of a medical polyoxypropylene polymer, comprising the following steps:
   (A) a step of adding to a polyoxypropylene polymer which is obtained by ring-opening polymerization of propylene oxide to a starting substance having an active hydrogen reacting with the propylene oxide and contains allyl ether as an impurity, a tertiary alkoxide of alkali metal in an excess amount based on a molar number of the active hydrogen of the starting substance and heat treating at 115° C. or less to isomerize the allyl ether to propenyl ether; and
   (B) a step of adding a mineral acid to the product obtained in the step (A) to adjust pH to 4 or less and treating at 70° C. or less to hydrolyze the propenyl ether.

2. The method as claimed in claim 1, performing after the step (B) described above, at least one of (C) a step of washing the polyoxypropylene polymer with water and (D) a step of treating the polyoxypropylene polymer with an inorganic adsorbent composed of an oxide containing at least one of aluminum and silicon.

3. A production method of a medical polyoxypropylene/polyoxyethylene block copolymer comprising a step of performing ring-opening polymerization of ethylene oxide to the polyoxypropylene polymer obtained by the method as claimed in claim 1.

4. A production method of a medical polyoxypropylene/polyoxyethylene block copolymer comprising a step of performing ring-opening polymerization of ethylene oxide to the polyoxypropylene polymer obtained by the method as claimed in claim 2.

* * * * *